(12) United States Patent
Abramovich et al.

(10) Patent No.: US 7,168,822 B2
(45) Date of Patent: Jan. 30, 2007

(54) RECONFIGURABLE LINESCAN ILLUMINATION

(75) Inventors: Gil Abramovich, Ann Arbor, MI (US); Zachary Warlick, Ann Arbor, MI (US); Yoram Koren, Ann Arbor, MI (US)

(73) Assignee: The Regents of the Univeristy of Michigan, Ann Arbor, MI (US)

( * ) Notice: Subject to any disclaimer, the term of this patent is extended or adjusted under 35 U.S.C. 154(b) by 228 days.

(21) Appl. No.: 10/978,805

(22) Filed: Nov. 1, 2004

(65) Prior Publication Data

US 2006/0091825 A1    May 4, 2006

(51) Int. Cl.
*F21V 33/00* (2006.01)

(52) U.S. Cl. ............... 362/250; 362/234; 362/287; 362/249; 359/707; 359/710

(58) Field of Classification Search ............... 362/234, 362/235, 249, 250, 285, 287, 418, 427; 359/599, 359/707, 708, 710
See application file for complete search history.

(56) References Cited

U.S. PATENT DOCUMENTS

| | | | |
|---|---|---|---|
| 4,620,768 A * | 11/1986 | Tatsuno et al. ............. 359/218 |
| 4,797,795 A | 1/1989 | Callahan |
| 4,893,223 A | 1/1990 | Arnold |
| 5,038,258 A | 8/1991 | Koch et al. |
| 5,309,277 A | 5/1994 | Deck |
| 5,453,849 A * | 9/1995 | Copenhaver et al. ....... 358/475 |
| 5,519,513 A * | 5/1996 | Copenhaver et al. ....... 358/475 |
| 6,161,941 A | 12/2000 | Tait et al. |
| 6,273,338 B1* | 8/2001 | White .................... 235/462.42 |
| 6,285,140 B1 | 9/2001 | Ruxton |
| 6,459,919 B1 | 10/2002 | Lys et al. |
| 6,624,597 B2 | 9/2003 | Dowling et al. |
| 6,713,746 B2 | 3/2004 | Veith et al. |
| 2005/0099795 A1* | 5/2005 | Seymour .................... 362/101 |

* cited by examiner

*Primary Examiner*—Thomas M. Sember
(74) *Attorney, Agent, or Firm*—Harness, Dickey & Pierce, P.L.C.

(57) ABSTRACT

A reconfigurable illumination system for illuminating an object, and associated method. The illumination system comprises a cylindrical diffuser having a longitudinal aperture, a linescan camera positioned for having a direct line of sight to the object through the aperture of the diffuser, a base, and an illuminator supported on the base and positioned between the diffuser and the object, wherein the illuminator is selectively reconfigurable in a plurality of configurations, each configuration corresponding to a manufacturing process that requires visual inspection of the object.

20 Claims, 11 Drawing Sheets

RECONFIGURABLE LINESCAN ILLUMINATION

FEDERALLY SPONSORED RESEARCH

Certain of the research leading to the present invention was sponsored by the United States Government under National Science Foundation Grant No. EEC-959125. The United States Government has certain rights in the invention.

INTRODUCTION

A machine vision system is typically a system able to extract data about a scene, using images captured by a camera. A scene is defined as part of the world which is within the visual field viewed by the camera. An image is a two-dimensional projection of a scene.

A machine vision system can be used for manufacturing processes to extract relevant information about the quality of a manufactured object or a manufacturing process. Illumination is an important component of any machine vision system because the ability of the system to capture images and extract data depends on the quality of the illumination.

Illumination can be categorized as "brightfield" or "darkfield". Brightfield illumination occurs where the camera is pointed at a region which is in the direct specular reflection from the illumination system. Darkfield illumination occurs where the camera is pointed at a region which is not in the direct specular reflection from the illumination system. In specific applications, brightfield or darkfield illumination and combinations thereof can be used to distinguish between regions of different reflection characteristics in the scene, which aids in recognizing boundaries, different materials, geometries or surface characteristics.

For maximum illumination efficiency and longevity, Light Emitting Diodes (LEDs) are often chosen as the illuminator and matched to the peak sensitivity wavelength of the camera sensor. Other light sources, such as a Halogen lamp combined with fiberoptic guides are common as well.

A linescan camera is a widely used sensor for industrial machine vision inspection systems. The linescan camera includes a one-dimensional sensor array, usually of the Charge Coupled Device (CCD) type. A high resolution frame is constructed by scanning the scene of interest and combining a predetermined number of lines into a frame. The scanning is enabled by a motion system which moves either the camera or the scene at a rate which matches the camera line rate. This camera type is common in industrial settings partly because a high-resolution image can be constructed using a relatively modest number of sensor elements. The linescan camera requires illumination of the strip of the inspected image frame captured by the camera. Different illumination solutions for linescan cameras are particularly challenging due to the high aspect ratio of the acquired line. As a result, different solutions are customized for particular applications.

There is, therefore, a need for an improved illumination system, which can handle different linescan illumination applications, and can reduce cost and integration time.

SUMMARY

The present teachings provide a reconfigurable illumination system for illuminating an object. The illumination system comprises a cylindrical diffuser having a longitudinal aperture, a linescan camera positioned for having a direct line of sight to the object through the aperture of the diffuser, a base, and an illuminator supported on the base and positioned between the diffuser and the object, wherein the illuminator is selectively reconfigurable in a plurality of configurations, each configuration corresponding to a manufacturing process that requires visual inspection of the object.

The present teachings also provide a method for illuminating an object. The method includes providing an illuminator having at least one axial light source, wherein the light source is movably supported on a base between a cylindrical diffuser having a longitudinal aperture and the object, positioning a linescan camera for direct line of sight to the object through the aperture of the diffuser, and selectively reconfiguring the illuminator in a plurality of configurations, wherein each configuration corresponds to a manufacturing process that requires visual inspection of the object.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. For example, although the present teachings are particularly illustrated for the manufacturing applications of surface defect inspection and dimension measurement, the present teachings can be used for machine vision or other visual inspection processes in the context of any manufacturing process.

Figure 1:
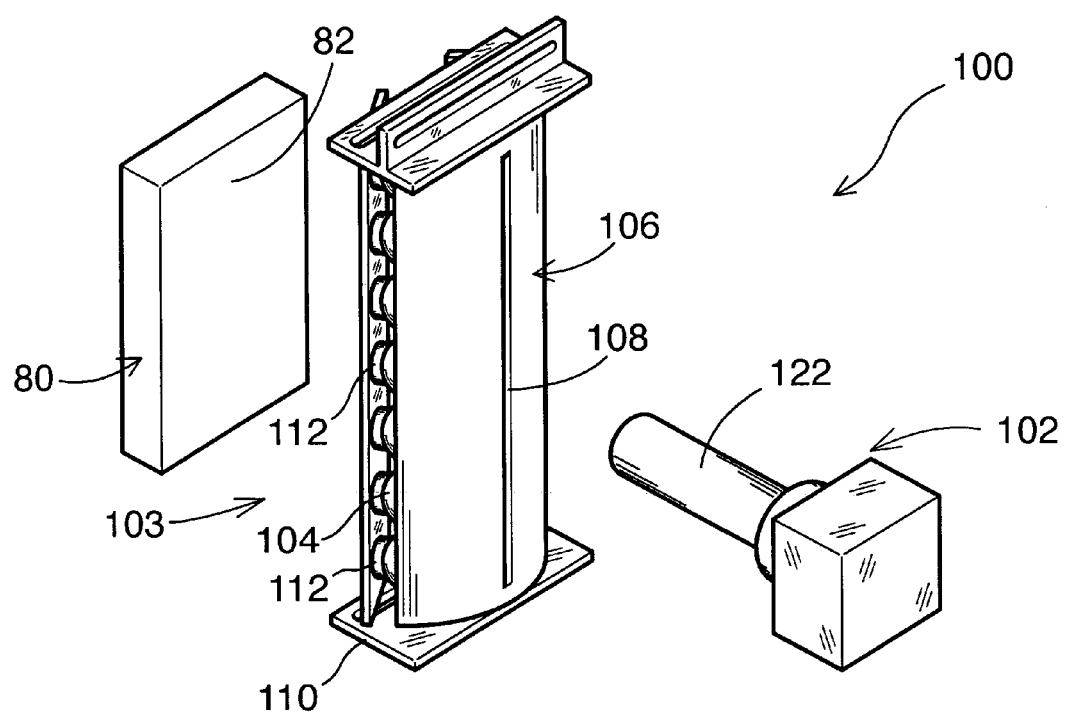
FIG. 1 is a perspective view of a reconfigurable illumination system according to the present teachings.
Figure 2:
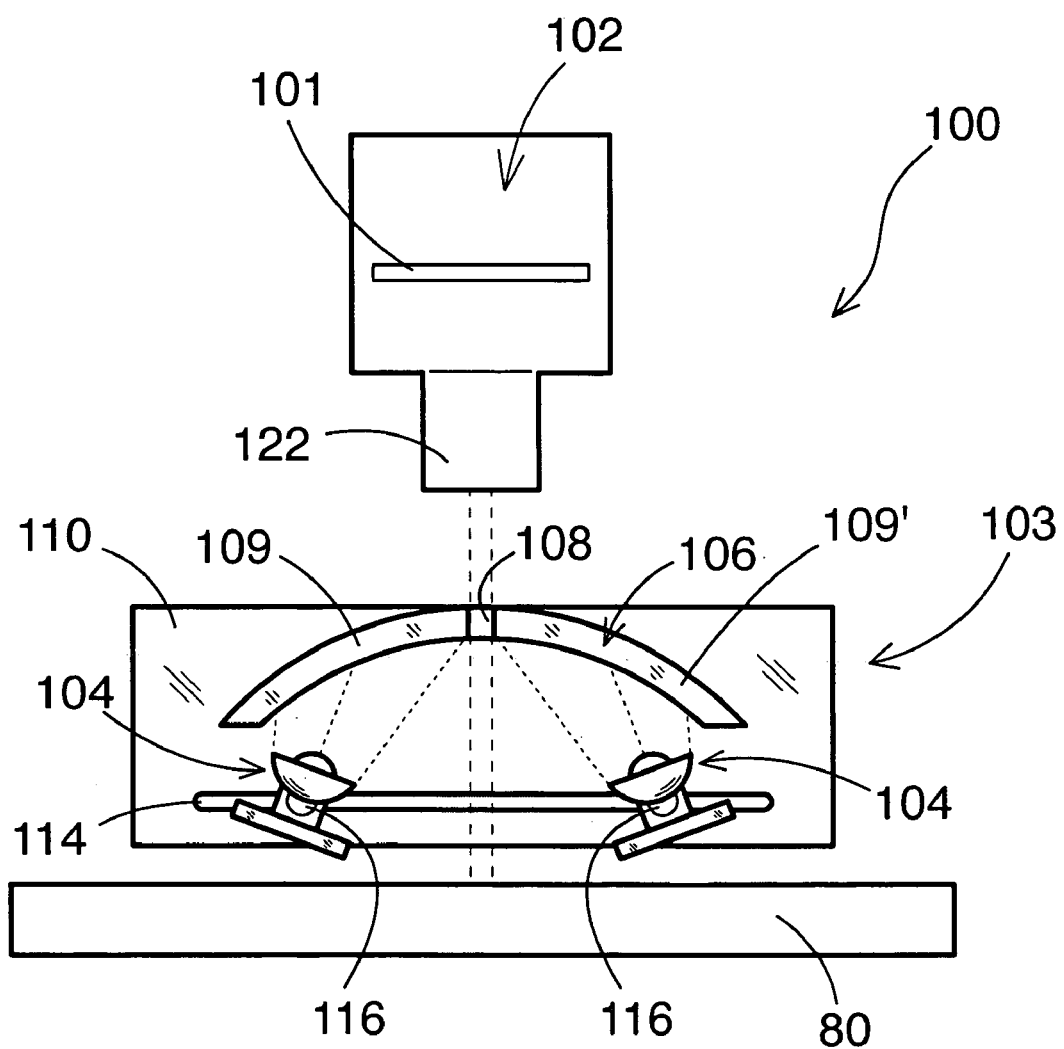
FIGS. 2–10 are plan views of the illumination system of FIG. 1, illustrating various illumination configurations according to the present teachings.

Referring to FIGS. 1 and 2, an exemplary reconfigurable illumination system 100 according to the present teachings may include a linescan camera 102 that has a lens 122 and a sensor array (or sensor) 101, an illuminator 103 that includes one or more light sources 104, and a cylindrical diffuser 106 that has a longitudinal aperture 108. The diffuser 106 can include two equal portions 109, 109' separated by the longitudinal aperture 108 through which the camera 102 views a surface 82 of a part or object 80. The diffuser 106 can be modular, such that the diffuser portions 109, 109' are movable relative to each other, and the aperture 108 can be selectively narrowed or widened, as desired in a particular application. Additionally, each diffuser portion 109, 109' can be completely removed from the diffuser 106, as desired.

The illuminator 103 can be modular such that the light sources 104 can be removed, as desired. The light sources 104 can be movably supported on a base 110 for allowing reconfiguration of the axial light sources 104, as desired for visual inspection of an object 80 in various manufacturing processes, as will be described below. Each light source 104 can include one or more illumination devices 112, such as LED, halogen, Xenon, and other illumination devices known in the art. The light source 104 can include, for example, a single illumination device 112 such as an individual spotlight, or an array of illumination devices 112 that form a linear or axial array (line light) or a broad area array that combines a plurality of linear arrays. FIG. 1 illustrates a light source 104 that comprises a linear (axial) array of LED illumination devices 112.

Referring to FIG. 2, each light source 104 can include a mount 116 that can be received in a track 114 of the base 110, such that the light source 104 can swivel 360° relative to the base 110 and can move along the track 114. Although the track 114 is shown as straight, it will be appreciated that the track can also be curved or otherwise shaped. To reconfigure each light source 104, the light source 104 can be rotated and/or translated along the track 114, and can also completely removed from the illuminator 103. Accordingly, each light source 104 can be directed to a desired area of the diffuser 106 or the object 80 to produce a desired degree of direct or diffuse illumination of the object 80 depending on the particular manufacturing application and the surface characteristics of the object 80. The light sources 104 can be independently controlled and can be reconfigured manually or by using any motorized control that is known in the art, including computer control.

FIGS. 2–10 illustrate various exemplary configurations of the reconfigurable illumination system 100 for various manufacturing processes related to machine vision, including but not limited to, dimensional measurement, inspection of defects on metallic surfaces and inspection of defects on non-metallic surfaces, for example.

Referring to FIG. 2, the light sources 104 can be configured symmetrically relative to the aperture 108, each light source 104 pointing to the portion 109, 109' of the diffuser 106 on the same side as the light source 104.

Figure 3:
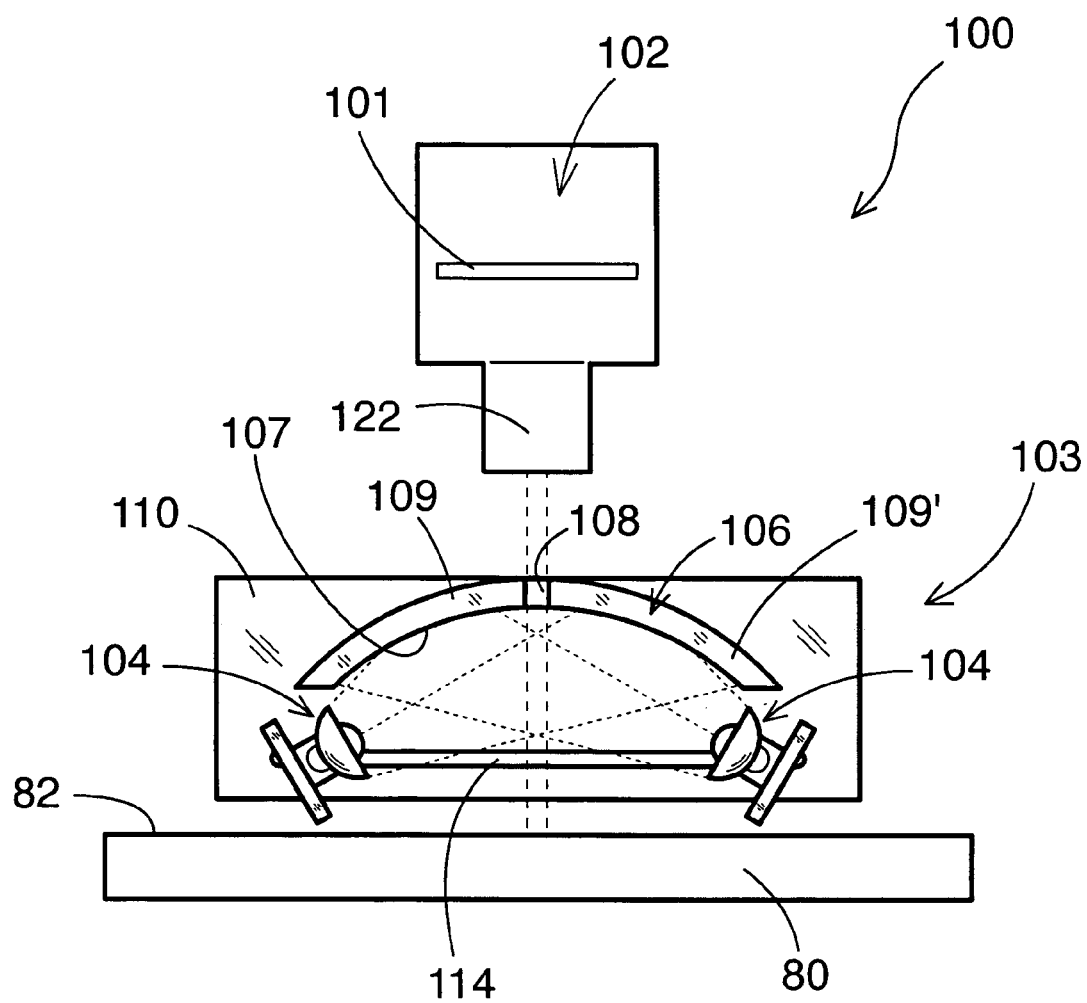

Referring to FIG. 3, the reconfigurable illumination system 100 can be configured for surface defect inspection of the surface 82 of the object 80. In the configuration of FIG. 3, the light sources 104 are rotated towards the inner surface 107 of the cylindrical diffuser 106. Each light source 104 is directed towards the portion 109, 109' of the diffuser 106 on the opposite side of the viewing aperture 108, diagonally opposite to the light source 104 relative to the aperture 108. The light sources 104 can be positioned at a distance and orientation that can be selected to provide peak illumination brightness in the camera field-of-view. The configuration of FIG. 3 also provides a uniform and diffuse illumination because of the large range of angles from which the surface 82 of the object 80 is irradiated (a range of over 90 degrees), reducing or eliminating shadows and allowing for almost isotropic-orientation illumination.

Figure 11:
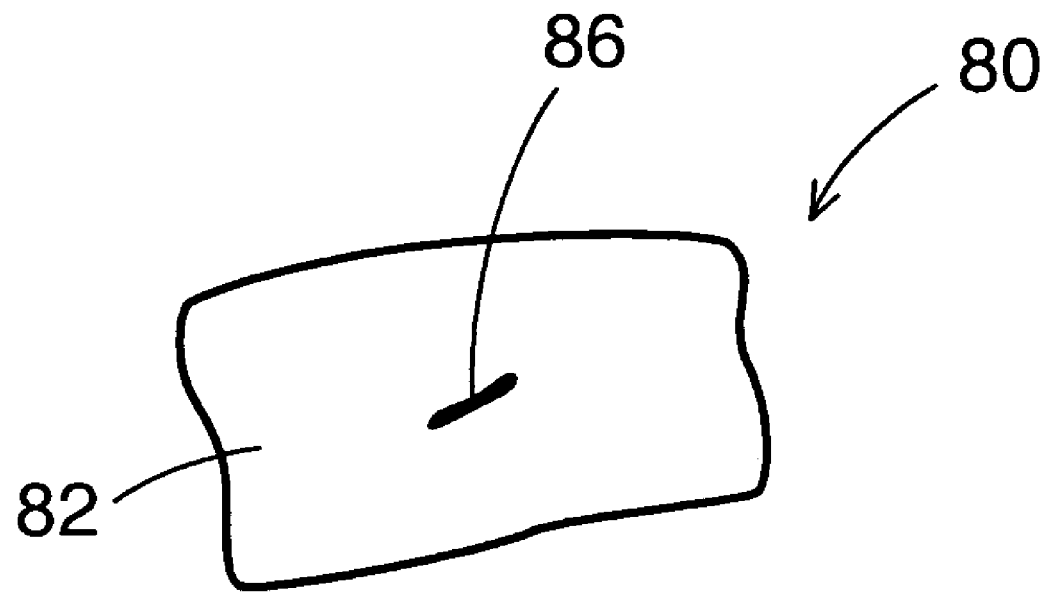
FIG. 11 is an illustration of a surface defect as detected according to the present teachings.

The configuration of FIG. 3 can be used for surface defect detection of metallic or shiny and textural surfaces 82. Referring to FIG. 11, the multiple illuminating directions provided by the configuration of FIG. 3 saturate with light the surface texture such that the surface texture appears as a white area, while deeper surface irregularities, such as pores and scratches 86, appear darker than the background since the inner/deep portions of the flaws do not have a line-of-sight to all the regions of the diffuser 106. Therefore, the configuration of FIG. 3 provides uniform illumination of the object 80 and saturates with light shallow part features, such as surface textural patterns of a machined metallic object 80, such that only deeper surface irregularities 86 stand out as darker areas.

Figure 4:
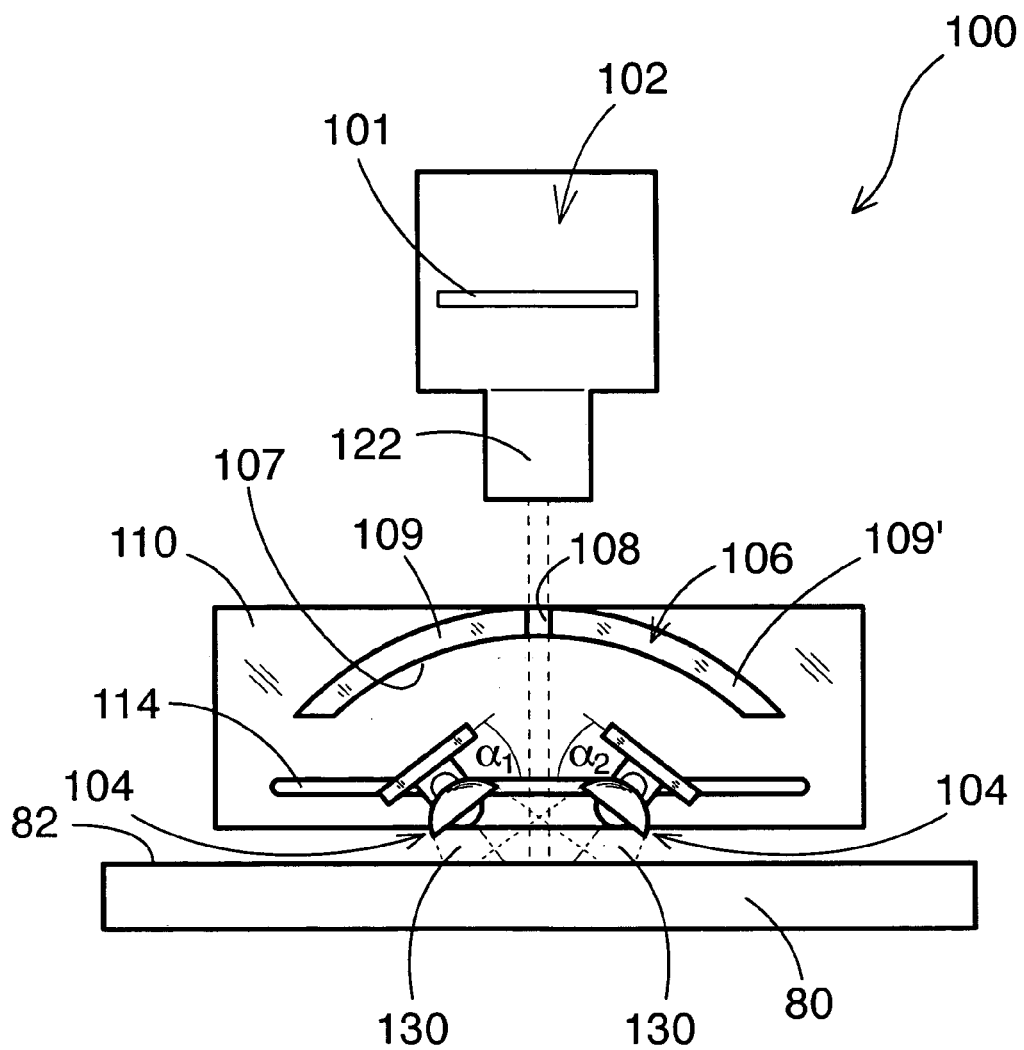

Referring to FIG. 4, the light sources 104 can be configured to be directed toward the surface 82 of the object at substantially opposite angles $\alpha_1$, $\alpha_2$ relative to the track 114, and such that respective light rays 130 intersect, producing a symmetric illumination.

Figure 5:
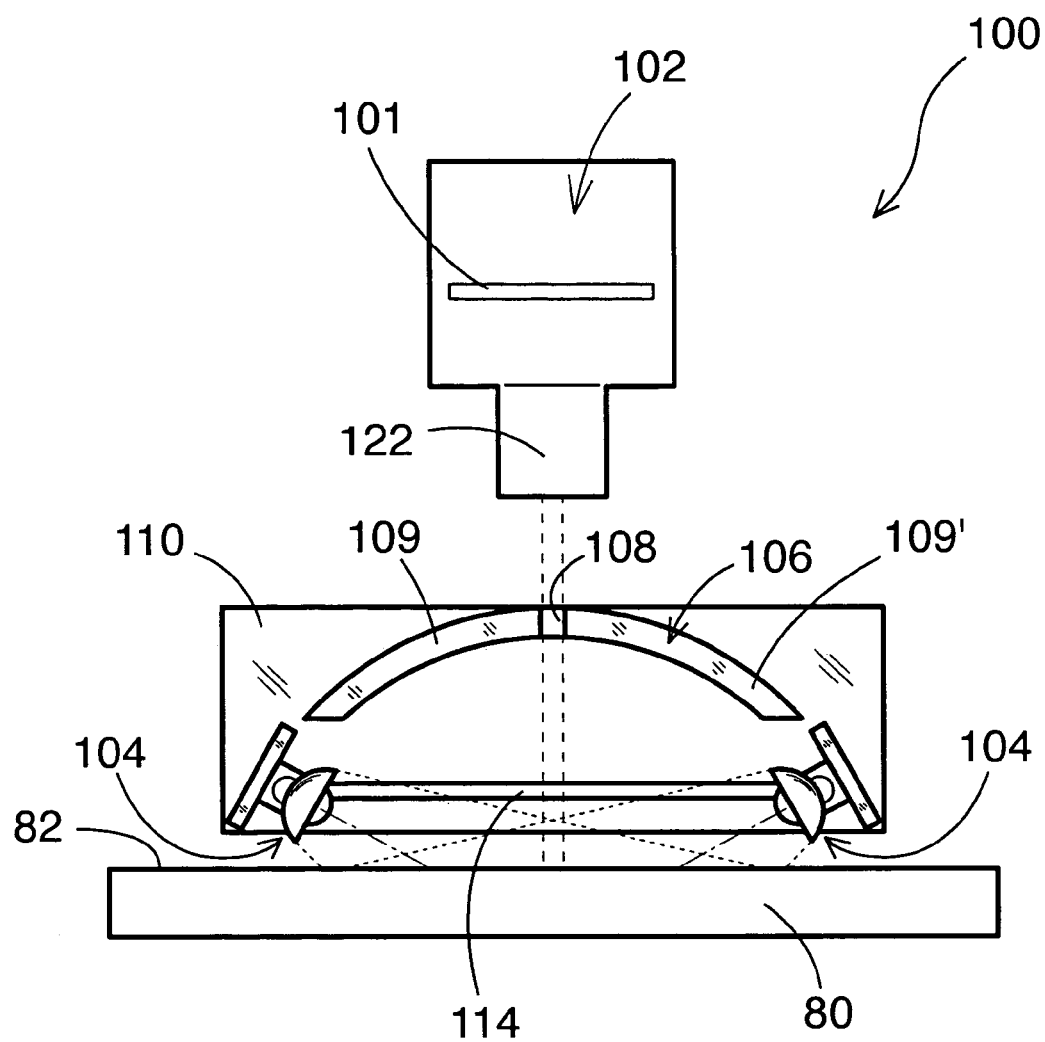

FIG. 5 is described below together with FIG. 10.

Figure 6:
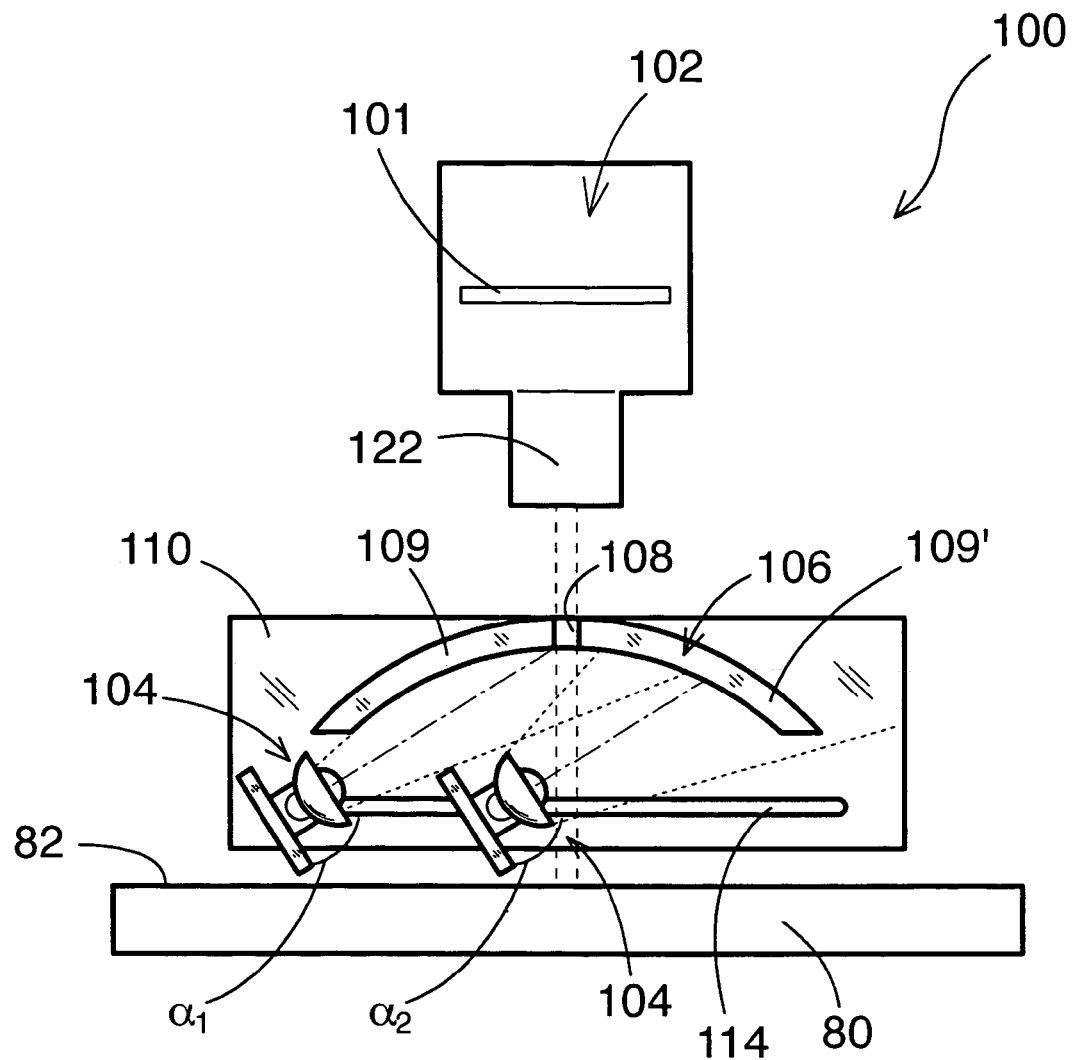

Referring to FIG. 6, the light sources 104 can be directed toward the diffuser 106 at substantially parallel angles $\alpha_1$, $\alpha_2$ relative to the track 114 producing an asymmetric diffuse illumination.

Figure 7:
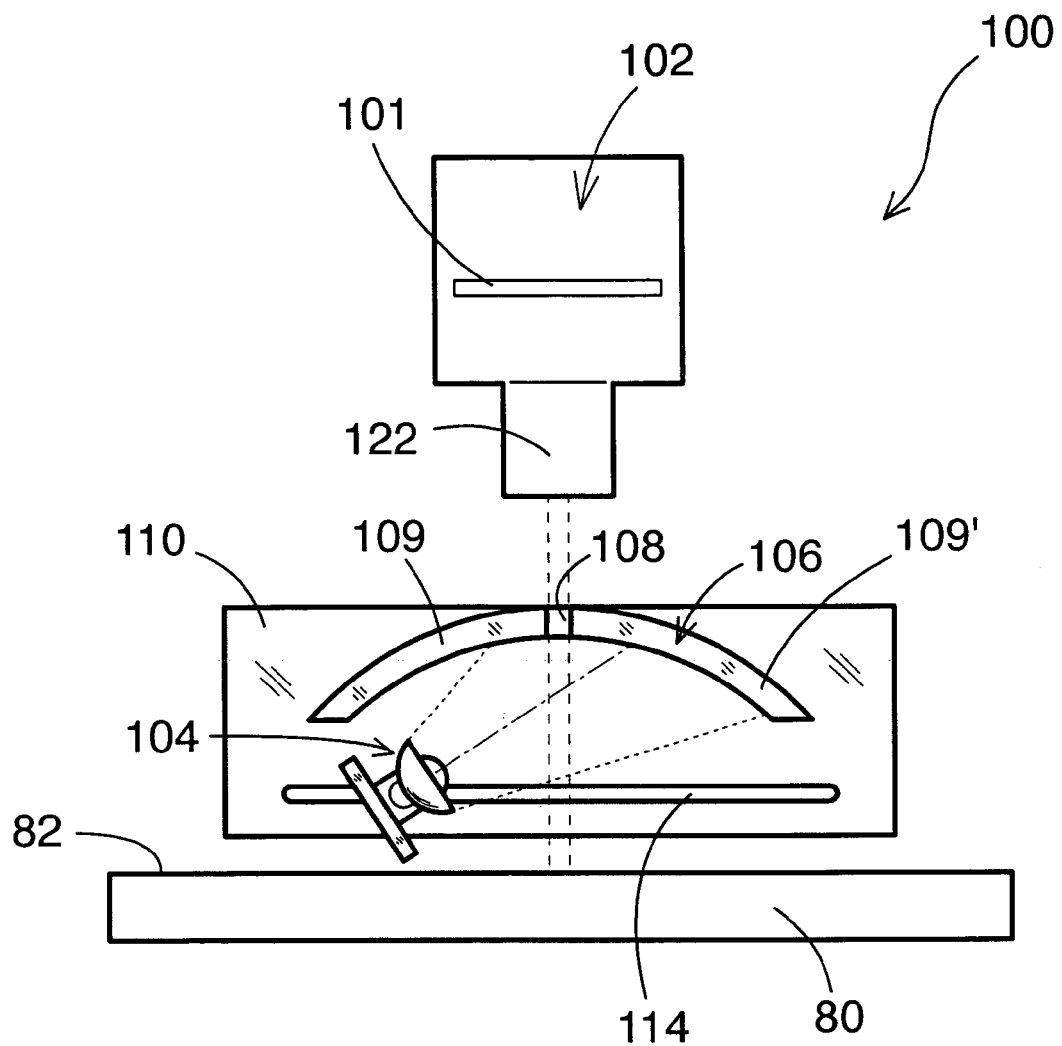

Referring to FIG. 7, a single light source 104 can be positioned at the same side as one portion 109 of the diffuser for pointing obliquely toward the other portion 109' of the diffuser 106, producing an asymmetric diffuse illumination.

Figure 8:
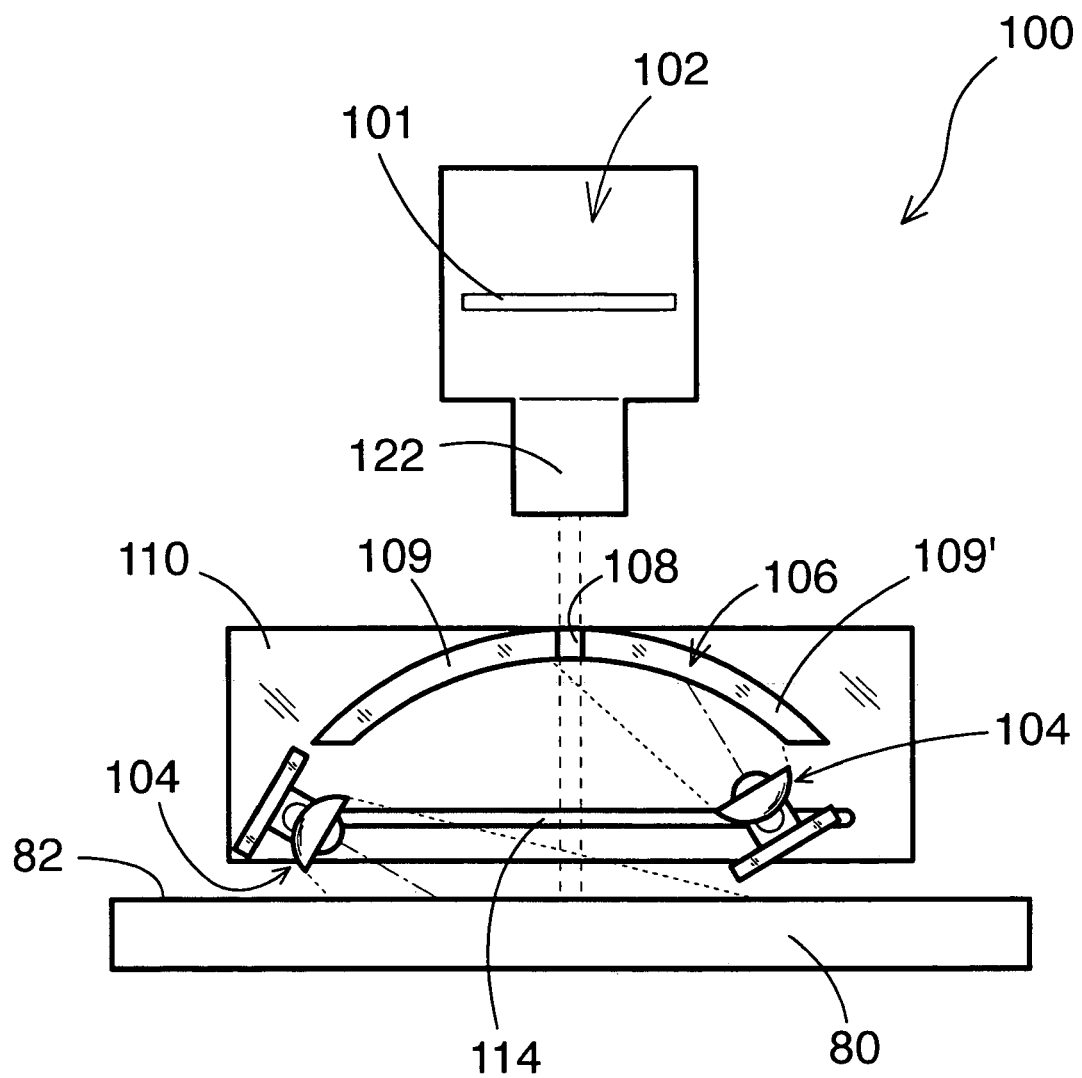

Referring to FIG. 8, one light source 104 can be directed obliquely toward the surface 82 of the object 80 and the other light source 104 can be directed obliquely toward the diffuser 106, producing a hybrid of direct and diffuse illumination.

Figure 9:
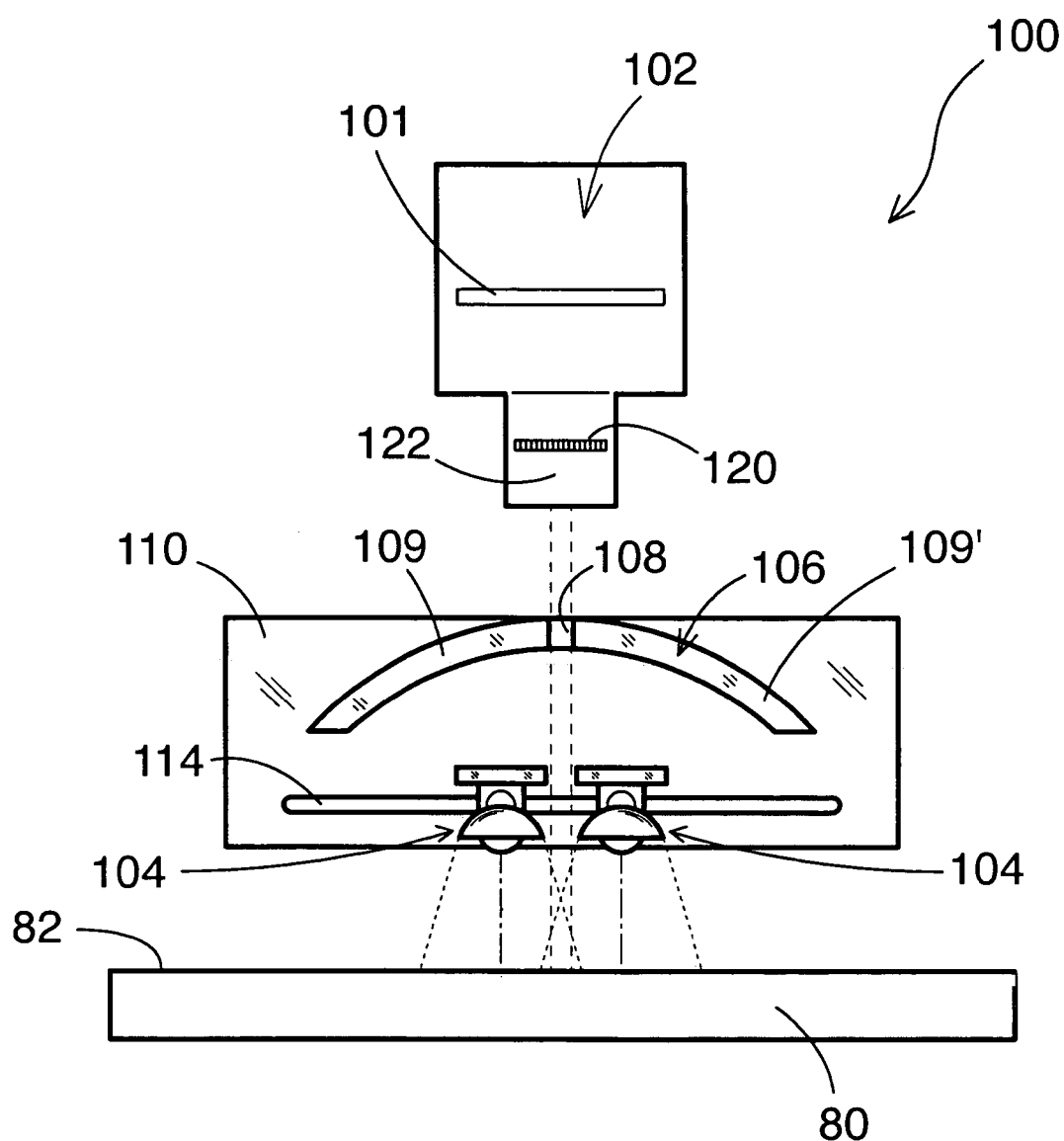

Referring to FIG. 9, the reconfigurable illumination system 100 is configured for dimensional measurement of the surface 82 of the object 80. In the configuration of FIG. 9, the portion of inspected surface 82 on the object 80 viewed by the camera 102 is within the direct illumination of the two light sources 104. The light sources 104 can be positioned close together, separated by the smallest distance that would allow a full view of the object 80 by the linescan camera 102. The configuration of FIG. 9 provides brightfield illumination of the object 80 and is suitable for dimensional measurement of non-shiny (matte) surfaces. Additionally, the configuration of FIG. 9 eliminates shadows and provides sharp images of the boundary edges of the object 80. A polarizer 120 may be used on the lens 122 of the camera 102 to improve performance for dimensional measurement, by reducing or eliminating undesirable specular reflection from the object 80.

In the configuration of FIG. 9, using an object-side telecentric lens 122 for the camera 102, can improve the effectiveness of the illumination system 100 by allowing only parallel rays to the camera axis to enter the lens 122, with minimal distortion and minimal effect of shadows on the perceived edge locations of the object 80 as viewed by the camera 102. As is known in the art, with object-side telecentric lenses the size of the viewed object 80 does not change when the distance between the object 80 and lens 122 varies. It is not necessary to use the more expensive both-sides telecentric lenses, in which the size of the object 80 does not change when both the distance between the object 80 and the lens 122, as well as the distance between the lens 122 and the sensor array 101 of the linescan camera 102 vary.

Figure 10:
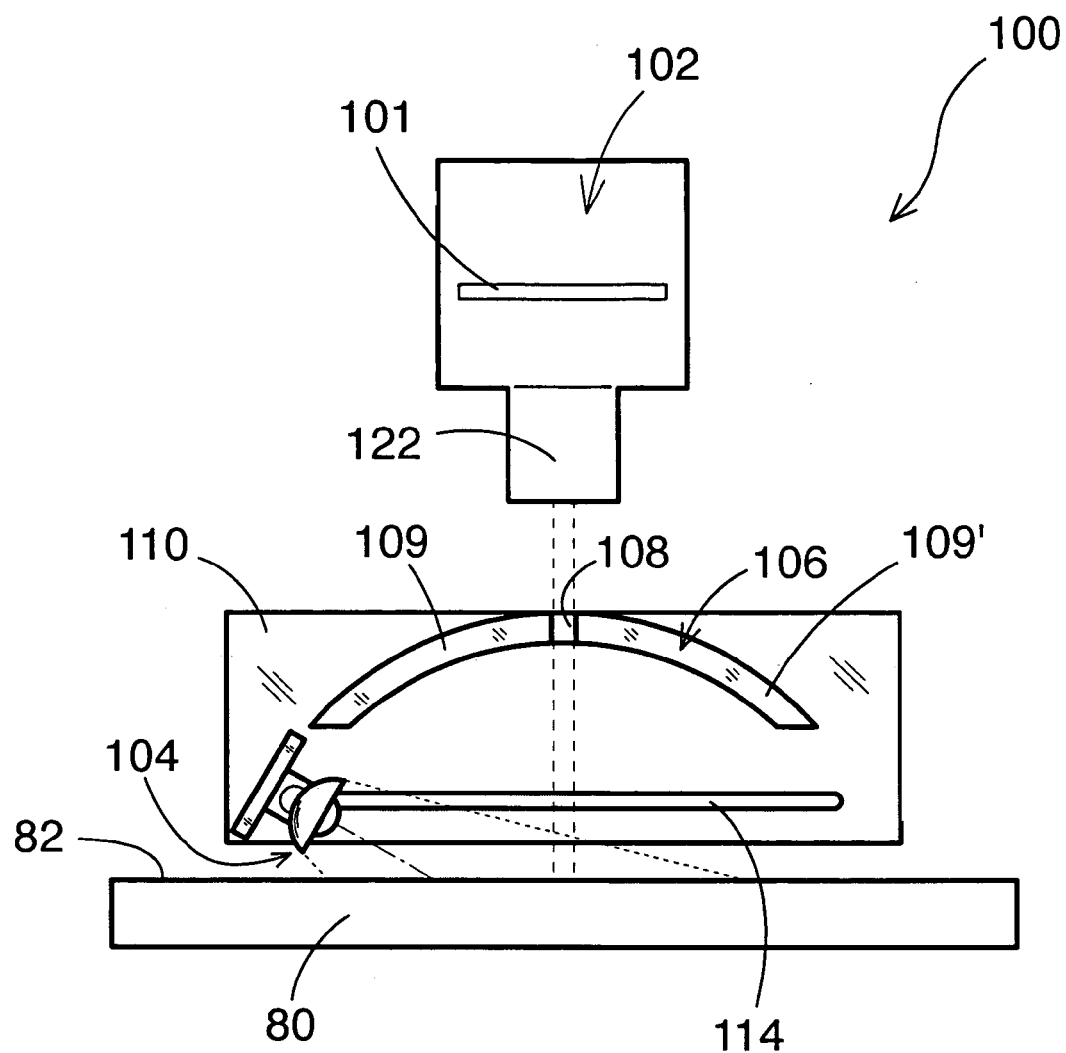

Referring to FIGS. 10 and 11, the reconfigurable illumination system 100 can be configured for surface defect inspection of non-textural surfaces 82. Illuminating the surface 82 of the object obliquely with a single light source 104 from one side saturates with light the surface 82, such that the surface 82 appears bright (white) in the image of the object 80. Irregularities, such as cavities and scratches 86, stand out as darker spots. Referring to FIG. 5, a variation of the configuration of FIG. 10 can include two symmetrically positioned light sources 104 illuminating obliquely the surface 82 of the object 80, wherein the light sources 104 can be operated at different time instances to produce two different images, potentially highlighting different features of the object 80. Integration of the two images or the data collected from the two images can improve flaw detection performance.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A reconfigurable illumination system for illuminating an object, the illumination system comprising:
   a cylindrical diffuser having a longitudinal aperture;
   a linescan camera positioned for having a direct line of sight to the object through the aperture of the diffuser;
   a base; and
   an illuminator supported on the base and positioned between the diffuser and the object, wherein the illuminator is selectively reconfigurable in a plurality of configurations, each configuration corresponding to a manufacturing process that requires visual inspection of the object.

2. The illumination system of claim 1, wherein the illuminator comprises first and second axial light sources, wherein the light sources configured for direct brightfield illumination of the object and wherein the manufacturing process comprises dimensional measurement of a non-shiny surface of the object.

3. The illumination system of claim 2, wherein the first and second light sources are configured to direct light perpendicularly to the object and parallel to the line of sight of the camera.

4. The illumination system of claim 3, wherein the light sources are configured to be positioned in close proximity relative to each other on opposite sides of the aperture.

5. The illumination system of claim 1, wherein the illuminator comprises two axial light sources configured for uniform and diffuse illumination, and the manufacturing process comprises surface defect inspection of a shiny textural surface of the object.

6. The illumination system of claim 5, wherein the light sources are spaced apart and are configured to direct light to portions of the diffuser which are diagonally opposite relative to the axial light sources.

7. The illumination system of claim 1, wherein the illuminator comprises at least one axial light source configured for bright illumination and the manufacturing process comprises surface defect inspection of a non textural surface of the object.

8. The illumination system of claim 7, wherein the axial source is configured for oblique illumination of the surface of the object.

9. A method for illuminating an object comprising:
   providing an illuminator having at least one axial light source, the light source movably supported on a base between a cylindrical diffuser having a longitudinal aperture and the object;
   positioning a linescan camera for direct line of sight to the object through the aperture of the diffuser; and
   selectively reconfiguring the illuminator in a plurality of configurations, each configuration corresponding to a manufacturing process that requires visual inspection of the object.

10. The method of claim 9, wherein reconfiguring the illuminator comprises moving the axial light source for direct brightfield illumination for dimensional measurement of a non shiny surface of the object.

11. The method of claim 9, wherein reconfiguring the illuminator comprises moving the axial light source for uniform and diffuse illumination for surface defect inspection of a shiny and textural surface of the object.

12. The method of claim 9, wherein reconfiguring the illuminator comprises moving the axial light source for bright and oblique illumination for surface defect inspection of a non-textural surface of the object.

13. The method of claim 9, wherein reconfiguring the illuminator comprises moving the light source along a track of the base.

14. The method of claim 13, wherein reconfiguring the illuminator further comprises rotating the light source relative to the base.

15. The method of claim 14, wherein reconfiguring the illuminator further comprises directing the light source toward a portion of the diffuser.

16. The method of claim 14, wherein reconfiguring the illuminator further comprises directing the light source toward a surface of the object.

17. The method of claim 9, wherein reconfiguring the illuminator comprises directing two light sources perpendicularly toward a surface of the object.

18. The method of claim 9, wherein reconfiguring the illuminator further comprises directing the light source toward a portion of the diffuser.

19. The method of claim 18, wherein the portion of the diffuser is diagonally opposite to the light source relative to the aperture.

20. The method of claim 9, wherein reconfiguring the illuminator comprises operating two light sources at different time instances.

* * * * *